United States Patent
Bradley et al.

(10) Patent No.: US 6,915,164 B2
(45) Date of Patent: Jul. 5, 2005

(54) AUTOMATIC CAPTURE USING INDEPENDENT CHANNELS IN BI-CHAMBER STIMULATION

(75) Inventors: Kerry Bradley, Glendale, CA (US); Joseph J. Florio, La Canada, CA (US); Gene A. Bornzin, Simi Valley, CA (US); Euljoon Park, Stevenson Ranch, CA (US)

(73) Assignee: Pacesetter, Inc., Sylmar, CA (US)

( * ) Notice: Subject to any disclaimer, the term of this patent is extended or adjusted under 35 U.S.C. 154(b) by 542 days.

(21) Appl. No.: 10/124,164

(22) Filed: Apr. 16, 2002

(65) Prior Publication Data

US 2003/0195579 A1 Oct. 16, 2003

(51) Int. Cl.⁷ .............................................. A61N 1/368
(52) U.S. Cl. ...................................................... 607/29
(58) Field of Search ............................ 607/4, 7, 9, 27, 607/28, 30

(56) References Cited

U.S. PATENT DOCUMENTS

| | | | |
|---|---|---|---|
| 4,928,688 A | 5/1990 | Mower ................. | 128/419 PG |
| 5,501,702 A | 3/1996 | Plicchi et al. ................. | 607/20 |
| 5,514,161 A | 5/1996 | Limousin ........................ | 607/9 |
| 5,720,768 A | 2/1998 | Verboven-Nelissen ......... | 607/9 |
| 5,792,203 A | 8/1998 | Schroeppel ................... | 607/30 |
| 5,800,465 A | 9/1998 | Thompson et al. ............ | 607/9 |
| 5,902,324 A | 5/1999 | Thompson et al. ............ | 607/9 |
| 6,081,748 A | 6/2000 | Struble et al. ................. | 607/9 |
| 6,122,545 A | 9/2000 | Struble et al. ................. | 607/9 |
| 6,128,535 A | 10/2000 | Maarse ........................ | 607/28 |
| 6,473,645 B1 * | 10/2002 | Levine ........................... | 607/9 |
| 6,512,953 B2 * | 1/2003 | Florio et al. .................. | 607/28 |
| 6,564,100 B2 * | 5/2003 | Warren et al. ................. | 607/28 |

FOREIGN PATENT DOCUMENTS

WO    WO 99/30777    6/1999    .......... A61N/1/368

* cited by examiner

Primary Examiner—George Manuel

(57) ABSTRACT

A cardiac stimulation device and method deliver independent stimulation pulses to right and left cardiac chambers, based on the capture thresholds of each chamber, and confirm capture in each chamber. A threshold test is performed in one chamber while stimulating the opposite chamber at increased pulse energy and adjusted interchamber delay.

40 Claims, 8 Drawing Sheets

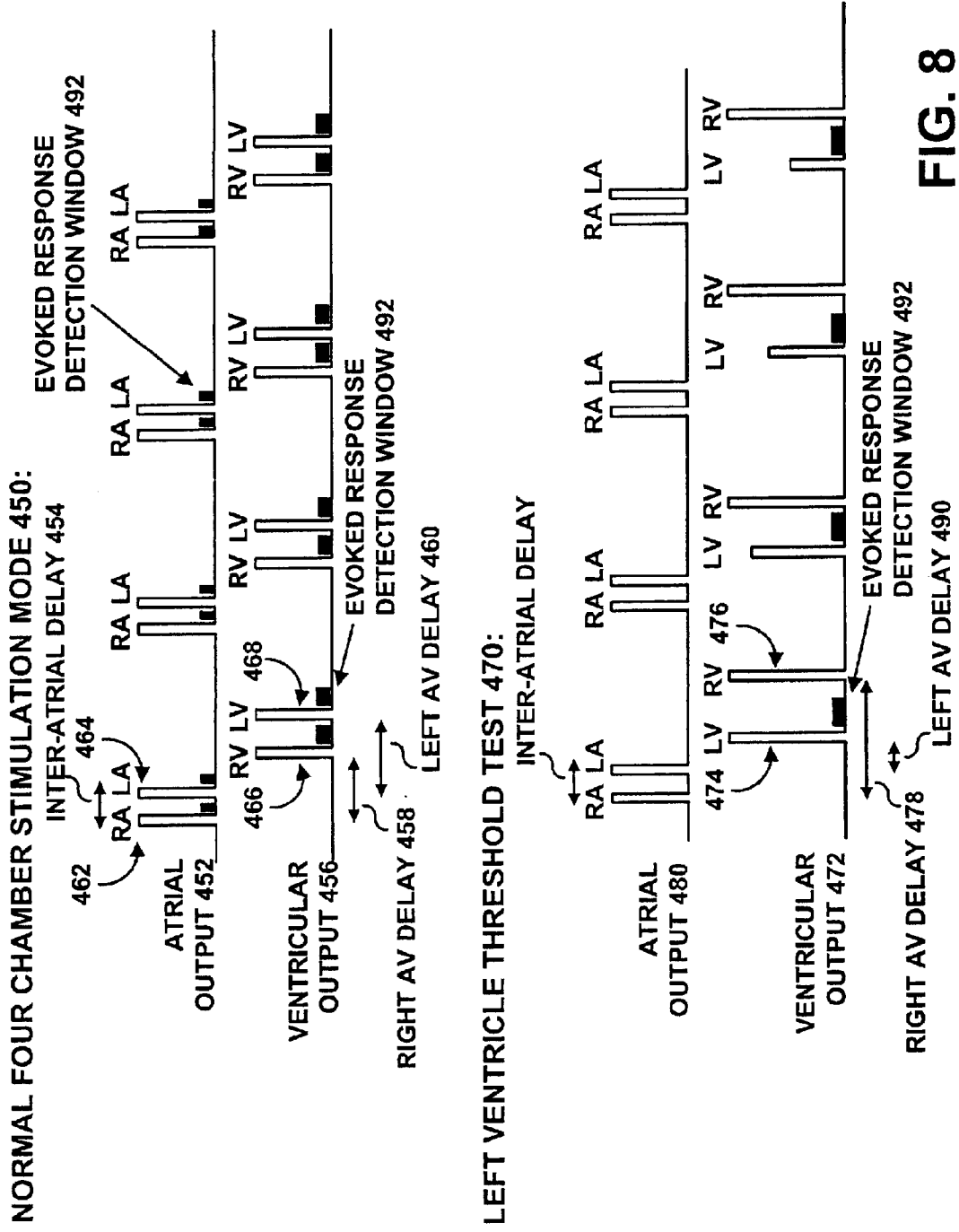

AUTOMATIC CAPTURE USING INDEPENDENT CHANNELS IN BI-CHAMBER STIMULATION

CROSS-REFERENCE TO RELATED APPLICATIONS

This application is related to copending U.S. application Ser. No. 09/904,159, filed Jul. 11, 2001, titled "System and Method for Programmably Controlling Stimulation Electrode Configurations and Activation Sequence in a Multi-Site Cardiac Stimulation Device."

FIELD OF THE INVENTION

The device relates to an implantable cardiac stimulation device that provides biatrial or biventricular stimulation therapy. More specifically, what is described is a method of automatically detecting and maintaining capture and performing threshold tests in each chamber individually during bi-chamber or multichamber stimulation.

BACKGROUND OF THE INVENTION

In the normal human heart, the sinus node, generally located near the junction of the superior vena cava and the right atrium, constitutes the primary natural pacemaker initiating rhythmic electrical excitation of the heart chambers. The cardiac impulse arising from the sinus node is transmitted to the two atrial chambers, causing a depolarization known as a P-wave and the resulting atrial chamber contractions. The excitation pulse is further transmitted to and through the ventricles via the atrioventricular (A-V) node and a ventricular conduction system causing a depolarization known as an R-wave and the resulting ventricular chamber contractions.

Disruption of this natural pacemaking and conduction system as a result of aging or disease can be successfully treated by artificial cardiac pacing using implantable cardiac stimulation devices, including pacemakers and implantable defibrillators, which deliver rhythmic electrical pulses or anti-arrhythmia therapies to the heart at a desired energy and rate. A cardiac stimulation device is electrically coupled to the heart by one or more leads possessing one or more electrodes in contact with the heart muscle tissue (myocardium). One or more heart chambers may be electrically stimulated depending on the location and severity of the conduction disorder.

A stimulation pulse delivered to the myocardium must be of sufficient energy to depolarize the tissue, thereby causing a contraction, a condition commonly known as "capture." In early pacemakers, a fixed, high-energy pacing pulse was delivered to ensure capture. While this approach is straightforward, it quickly depletes battery energy and can result in patient discomfort due to extraneous stimulation of surrounding skeletal muscle tissue.

"Threshold" is defined as the lowest stimulation pulse energy at which capture occurs. By stimulating the heart chambers at or just above threshold, comfortable and effective cardiac stimulation is provided without unnecessary depletion of battery energy. Threshold, however, is extremely variable from patient-to-patient due to variations in electrode systems used, electrode positioning, physiological and anatomical variations of the heart itself, and so on. Furthermore, threshold will vary over time within a patient as, for example, fibrotic encapsulation of the electrode occurs during the first few weeks after surgery. Fluctuations may even occur over the course of a day or with changes in medical therapy or disease state.

Hence, techniques for monitoring the cardiac activity following delivery of a stimulation pulse have been incorporated in modern pacemakers in order to verify that capture has indeed occurred. If a loss of capture is detected by such "capture-verification" algorithms, a threshold test is performed by the cardiac pacing device in order to re-determine the threshold and automatically adjust the stimulating pulse energy. This approach, called "automatic capture", improves the cardiac stimulation device performance in at least two ways: 1) by verifying that the stimulation pulse delivered to the patient's heart has been effective, and 2) greatly increasing the device's battery longevity by conserving the battery charge used to generate stimulation pulses.

Commonly implemented techniques for verifying that capture has occurred involve monitoring the internal electrocardiogram (IEGM) signals received on the implanted cardiac electrodes. When a stimulation pulse is delivered to the heart, the IEGM signals that are manifest concurrent with depolarization of the myocardium are examined. When capture occurs, an "evoked response" may be detected, which is seen as the intracardiac P-wave or R-wave on the IEGM that indicates contraction of the respective cardiac tissue. Through sampling and signal processing algorithms, the presence of an evoked response following a stimulation pulse is determined. For example, if a stimulation pulse is applied to the ventricle, an R-wave sensed by ventricular sensing circuits of the pacemaker immediately following application of the ventricular stimulation pulse evidences capture of the ventricles.

If no evoked response is detected, typically a high-energy back-up stimulation pulse is delivered to the heart within a short period of time in order to prevent asystole. An automatic threshold test is next invoked in order to re-determine the minimum pulse energy required to capture the heart. An exemplary automatic threshold determination procedure is performed by first increasing the stimulation pulse output level to a relatively high predetermined testing level at which capture is certain to occur. Thereafter, the output level is progressively decremented until capture is lost. The stimulation pulse energy is then set to a level safely above the lowest output level at which capture was attained. Thus, reliable capture verification is of utmost importance in proper determination of the threshold.

Conventional cardiac stimulation devices include single-chamber, or bi-chamber pacemakers or implantable defibrillators. A single-chamber device is used to deliver stimulation to only one heart chamber, typically the right atrium or the right ventricle. A bi-chamber stimulation device is used to stimulate both an atrial and ventricular chamber, for example the right atrium and the right ventricle. It has become apparent in clinical practice that the timing interval between atrial stimulation and ventricular stimulation, known as the AV interval or AV delay, may be important in achieving the desired benefit of bi-chamber pacing. Hence, capture verification in each chamber is important in maintaining the desired atrial-ventricular synchrony.

Mounting clinical evidence now supports the evolution of cardiac stimulating devices capable of stimulating both the left and right heart chambers, e.g., the left and right atrium or the left and right ventricle, or even three or all four heart chambers. Therapeutic applications indicated for bi-chamber (left and right heart chamber) stimulation or multi-chamber stimulation include stabilization of arrhythmias or re-synchronization of heart chamber contractions in patients suffering from congestive heart failure. The precise synchronization of the left and right heart chamber depolarizations is expected to be important in achieving the desired hemodynamic or anti-arrhythmic benefit. Thus, verifying capture in each chamber being stimulated would be essential in maintaining the desired stimulation benefit.

However, in order to achieve bi-chamber or multi-chamber stimulation in a clinical setting, conventional pacemakers have sometimes been used in conjunction with an adapter or a special bifurcated lead so that electrodes may be positioned in both the left and right heart chambers with electrical communication via only one lead connection to the same output channel of the stimulation device.

A four chamber pacing system has been proposed in which unipolar right and left atrial leads are connected via a bifurcated bipolar adapter to the atrial port of a bipolar dual chamber pacemaker. Likewise, unipolar right and left ventricular leads are connected via a bifurcated bipolar adapter to the ventricular channel. The left chamber leads are connected to the anode terminals and the right chamber leads are connected to the cathode terminals of the dual chamber device. In this way, simultaneous bi-atrial or simultaneous bi-ventricular pacing is achieved via bipolar stimulation but with several limitations.

One limitation is that simultaneous stimulation of left and right chambers, as required when two leads are coupled together by one adapter, or by internal hardwiring, is not always desirable. First, such a configuration is sub-optimal in terms of energy delivery because the right chamber lead acts as an additional load during left chamber stimulation and the left chamber lead acts as an additional load during right chamber stimulation.

Second, when inter-atrial or inter-ventricular conduction is intact, stimulation in one chamber may be conducted naturally to depolarize the second chamber. A stimulation pulse delivered in one chamber, using the minimum energy required to depolarize that chamber, often is conducted to the opposing chamber, thereby depolarizing both chambers. In this case, stimulation of both chambers would be wasteful of battery energy.

Precise control of the depolarization sequence and timing may be necessary in order to provide the anti-arrhythmic or hemodynamic support desired. Multi-chamber stimulation systems have been proposed that allow independent stimulation in each chamber, in some cases related to a coupling interval based on sensed or paced events in other chambers.

In order to ensure and maintain a desired depolarization sequence, performing capture verification in each chamber being stimulated is essential. One proposed method of performing capture verification during multisite cardiac pacing verifies capture in one area of the heart by detecting a conducted depolarization in another area of the heart that is electrically continuous with the stimulated area. The limitation of such a method is that it relies on the natural conduction of the depolarization within the cardiac tissue.

In bi-chamber or multi-chamber stimulation, the inter-chamber conduction may not be intact, or stimulation of both chambers may be preferred at a prescribed interval rather than waiting for a naturally conducted depolarization to travel from one chamber to the opposing chamber. Immediate detection of the local evoked response in the chamber being stimulated would be necessary in these situations. As a result, the proposed method would not be appropriate in all patients.

There remains an unmet need for a bi-chamber or multi-chamber cardiac stimulation device that allows independent stimulation and sensing in both right and left chambers of the heart and further provides reliable capture verification in each chamber. It would thus be desirable to provide a system and method for bi-chamber or multi-chamber stimulation with capture verification and automatic threshold determination made possible in each chamber independently.

SUMMARY OF THE INVENTION

An implantable bi-chamber or multi-chamber cardiac stimulation device is described that is capable of performing independent capture verification and threshold measurements in each chamber. A feature of the device is to verify that separate stimulation pulses delivered to the left and the right heart chambers, either atrial or ventricular, effectively capture the intended chamber in order to ensure a desired sequence of activation between the left and right chambers. Another feature of the device is to provide stimulation of each chamber according to its own capture threshold in order to conserve battery longevity.

In a preferred embodiment, the control system controls the delivery of stimulation pulses to the left and right heart chambers (atria or ventricles) at prescribed interchamber delays. Stimulation pulses are delivered by independent output channels such that each chamber receives stimulation pulses according to the capture threshold for that chamber. The capture threshold for each chamber is determined by performing independent threshold tests in each chamber periodically or in response to a loss of capture detection. Capture verification following the delivery of a stimulation pulse is verified by sensing the local evoked response. If loss of capture is detected, a threshold test is performed to allow adjustment of the stimulation pulse energy if the capture threshold has increased.

In one embodiment, a threshold test during biatrial or biventricular stimulation is performed in one chamber while stimulating the opposite chamber at an extended interchamber delay and at an increased pulse energy guaranteed to ensure capture of the opposite chamber. If all four heart chambers are stimulated, and atrioventricular conduction is intact, ventricular threshold tests are performed in one ventricle at a time while the stimulation pulse energy and atrial-ventricular delays to the opposite chamber are temporarily adjusted.

The adjusted interchamber delay is used to prevent a stimulation pulse delivered in the opposite chamber from causing interference during an evoked response detection window in the tested chamber and to prevent a conducted depolarization from the opposite chamber from interfering with evoked response detection in the tested chamber.

The increased stimulation pulse output in the opposite chamber ensures capture of the opposite chamber, which allows a depolarization to be conducted back to the tested in chamber in case a threshold test pulse does not capture the test chamber. In this way, a back-up stimulation pulse may not be needed in the tested chamber. After completing a threshold test in the first chamber, a threshold test may be performed in the opposite chamber while stimulating the first chamber at an extended interchamber delay and increased stimulation pulse output.

In another embodiment, the threshold testing may be performed concurrently in both the right and left chambers. Simultaneous stimulation pulses are delivered followed by sensing for an evoked response in each chamber during a designated evoked response detection window that expires before a conducted depolarization from the opposite chamber could interfere with local evoked response detection.

The methods and devices disclosed ensure the full benefit of bi-chamber or multichamber stimulation by verifying capture in each chamber in response to independent stimulation pulses delivered at prescribed interchamber delays. Independent stimulation of each chamber further improves battery longevity of the stimulation device since leads to both left and right chambers are not loading a single output channel.

DETAILED DESCRIPTION OF THE DRAWINGS

The various features of the devices and methods and the manner of attaining them will be described in greater detail with reference to the following description, claims, and drawings, wherein reference numerals are reused, where appropriate, to indicate a correspondence between the referenced items, and wherein:

FIG. 8 is an illustration of the output generated by the device of FIG. 2 during the implementation of the method of FIG. 7.

DETAILED DESCRIPTION OF THE PREFERRED EMBODIMENTS

The following description is of a best mode presently contemplated for practicing the invention. This description is not to be taken in a limiting sense but is made merely for the purpose of describing the general principles of the invention. In the description of the invention that follows, like numerals or reference designators will be used to refer to like parts or elements throughout. The device and method are directed at providing automatic capture in an implantable cardiac stimulating device possessing pacemaking, cardioversion and defibrillation capabilities. A general cardiac stimulation device will thus be described in conjunction with FIGS. 1 and 2, in which the automatic capture feature of the device could be implemented. It is recognized, however, that numerous variations of such a device exist in which the methods could be implemented.

Figure 1:
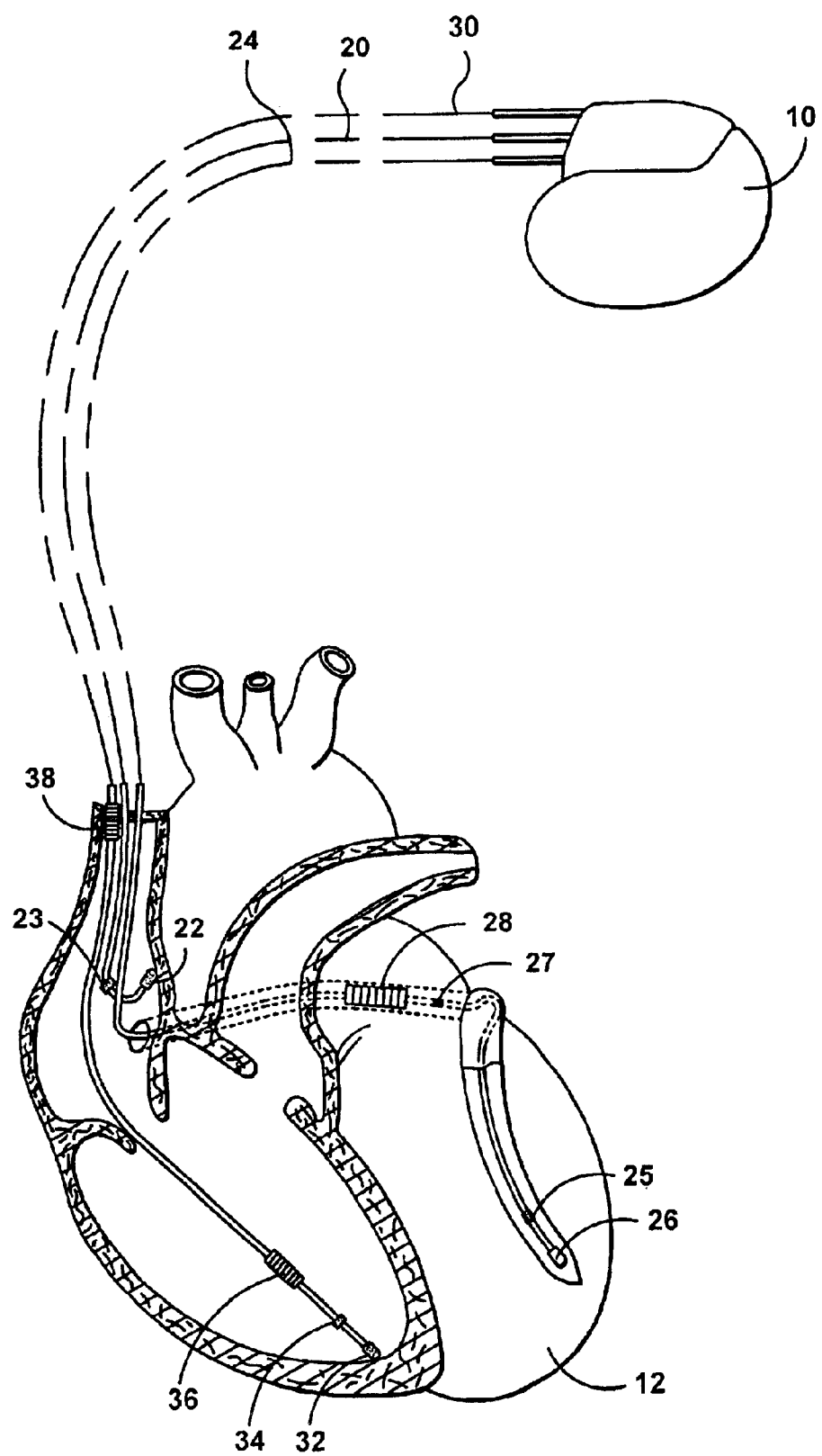
FIG. 1 is a simplified, partly cutaway view illustrating an implantable stimulation device in electrical communication with at least three leads implanted into a patient's heart for delivering multi-chamber stimulation and shock therapy.

FIG. 1 illustrates a stimulation device 10 in electrical communication with a patient's heart 12 by way of three leads 20, 24 and 30 suitable for delivering multi-chamber stimulation and shock therapy. To sense atrial cardiac signals and to provide right atrial chamber stimulation therapy, the stimulation device 10 is coupled to an implantable right atrial lead 20 having at least an atrial tip electrode 22, which typically is implanted in the patient's right atrial appendage. The right atrial lead 20 may also have an atrial ring electrode 23 to allow bipolar stimulation or sensing in combination with the atrial tip electrode 22.

To sense the left atrial and ventricular cardiac signals and to provide left-chamber stimulation therapy, the stimulation device 10 is coupled to a "coronary sinus" lead 24 designed for placement in the "coronary sinus region" via the coronary sinus ostium so as to place a distal electrode adjacent to the left ventricle and additional electrode(s) adjacent to the left atrium. As used herein, the phrase "coronary sinus region" refers to the vasculature of the left ventricle, including any portion of the coronary sinus, great cardiac vein, left marginal vein, left posterior ventricular vein, middle cardiac vein, and/or small cardiac vein or any other cardiac vein accessible by the coronary sinus.

Accordingly, the coronary sinus lead 24 is designed to receive atrial and ventricular cardiac signals and to deliver left ventricular pacing therapy using: at least a left ventricular tip electrode 26 for unipolar configurations or in combination with left ventricular ring electrode 25 for bipolar configurations; left atrial pacing therapy using at least a left atrial ring electrode 27, and shocking therapy using at least a left atrial coil electrode 28.

The stimulation device 10 is also shown in electrical communication with the patient's heart 12 by way of an implantable right ventricular lead 30 having, in this embodiment, a right ventricular tip electrode 32, a right ventricular ring electrode 34, a right ventricular (RV) coil electrode 36, and a superior vena cava (SVC) coil electrode 38. Typically, the right ventricular lead 30 is transvenously inserted into the heart 12 so as to place the right ventricular tip electrode 32 in the right ventricular apex so that the RV coil electrode 36 will be positioned in the right ventricle and the SVC coil electrode 38 will be positioned in the right atrium and/or superior vena cava. Accordingly, the right ventricular lead 30 is capable of receiving cardiac signals, and delivering stimulation in the form of pacing and shock therapy to the right ventricle.

Figure 2:
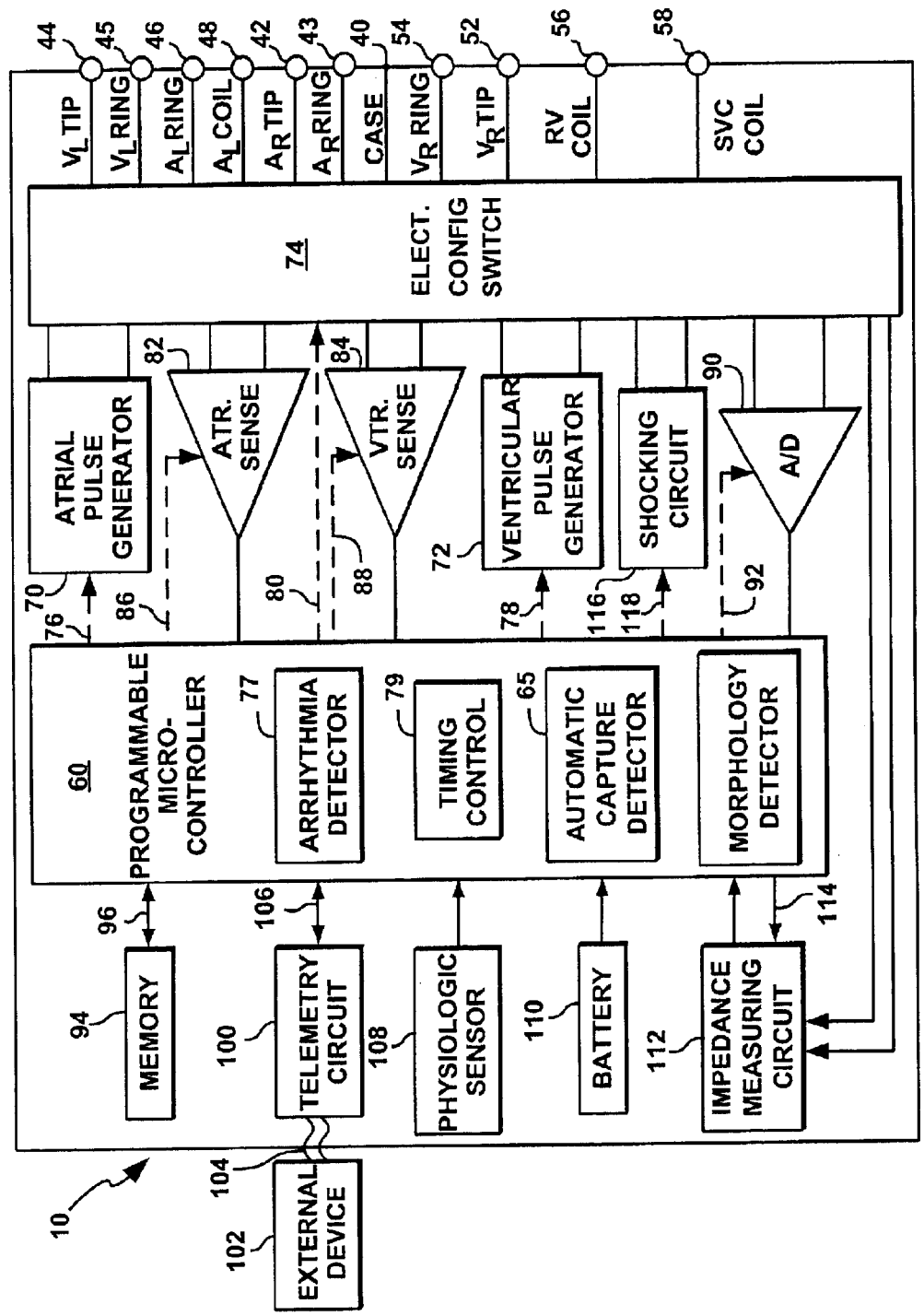
FIG. 2 is a functional block diagram of the multi-chamber implantable stimulation device of FIG. 1, illustrating the basic elements that provide pacing stimulation, cardioversion, and defibrillation in four chambers of the heart.

FIG. 2 illustrates a simplified block diagram of the multi-chamber implantable stimulation device 10, which is capable of treating both fast and slow arrhythmias with stimulation therapy, including cardioversion, defibrillation, and pacing stimulation. While a particular multi-chamber device is shown, this is for illustration purposes only, and one of skill in the art could readily duplicate, eliminate or disable the appropriate circuitry in any desired combination to provide a device capable of treating the appropriate chamber(s) with cardioversion, defibrillation and pacing stimulation.

The stimulation device 10 includes a housing 40 which is often referred to as "can", "case" or "case electrode", and which may be programmably selected to act as the return electrode for all "unipolar" modes. The housing 40 may further be used as a return electrode alone or in combination with one or more of the coil electrodes 28, 36, or 38, for defibrillation shocking purposes. The stimulation device 40 further includes a connector having a plurality of terminals 42, 43, 44, 45, 46, 48, 52, 54, 56, and 58 (shown schematically and, for convenience, the names of the electrodes to which they are connected are shown next to the corresponding terminals). As such, to achieve right atrial sensing and stimulation, the connector includes at least a right atrial tip terminal ($A_R$ TIP) 42 adapted for connection to the atrial tip electrode 22. The connector may also include a right atrial ring terminal ($A_R$ RING) 43 for connection to the atrial ring electrode 23.

To achieve left chamber sensing, pacing, and shocking, the connector includes at least a left ventricular tip terminal ($V_L$ TIP) 44, a left ventricular ring terminal ($V_L$ RING) 45, a left atrial ring terminal ($A_L$ RING) 46, and a left atrial shocking coil terminal ($A_L$ COIL) 48, which are adapted for connection to the left ventricular tip electrode 26, the left ventricular ring electrode 25, the left atrial ring electrode 27, and the left atrial coil electrode 28, respectively.

To support right ventricular sensing, pacing and shocking, the connector further includes a right ventricular tip terminal ($V_R$ TIP) 52, a right ventricular ring terminal ($V_R$ RING) 54, a right ventricular shocking coil terminal (RV COIL) 56, and an SVC shocking coil terminal (SVC COIL) 58, which are adapted for connection to the right ventricular tip electrode 32, right ventricular ring electrode 34, the RV coil electrode 36, and the SVC coil electrode 38, respectively.

At the core of the stimulation device 10 is a programmable microcontroller 60 that controls the various modes of stimulation therapy. The microcontroller 60 typically includes a microprocessor, or equivalent control circuitry, designed specifically for controlling the delivery of stimulation therapy, and may further include RAM or ROM memory, logic and timing circuitry, state machine circuitry, and I/O circuitry. Typically, the microcontroller 60 includes the ability to process or monitor input signals (data) as controlled by a program code stored in a designated block of memory. Any suitable microcontroller 60 may be used that carries out the functions described herein.

FIG. 2 illustrates an atrial pulse generator 70 and a ventricular pulse generator 72 that generate stimulation pulses for delivery by the right atrial lead 20, the right ventricular lead 30, and/or the coronary sinus lead 24 via a switch 74. It is understood that in order to provide stimulation therapy in each of the four chambers of the heart, the atrial pulse generator 70 and the ventricular pulse generator 72 may include dedicated, independent pulse generators, multiplexed pulse generators, or shared pulse generators. In accordance with the device, independent output channels are provided for each heart chamber to undergo stimulation in order to achieve independent stimulation of the right and left atrial or ventricular chambers. The atrial pulse generator 70 and the ventricular pulse generator 72 are controlled by the microcontroller 60 via appropriate control signals 76 and 78, respectively, to trigger or inhibit the stimulation pulses.

The microcontroller 60 further includes timing control circuitry 79 which is used to control the timing of such stimulation pulses (e.g., pacing rate, atrio-ventricular (AV) delay, atrial interchamber (A—A) delay, or ventricular interchamber (V—V) delay, etc.), as well as to keep track of the timing of refractory periods, PVARP intervals, noise detection windows, evoked response windows, alert intervals, marker channel timing, etc.

The switch 74 includes a plurality of switches for connecting the desired electrodes to the appropriate I/O circuits, thereby providing complete electrode programmability. Accordingly, the switch 74, in response to a control signal 80 from the microcontroller 60, determines the polarity of the stimulation pulses (e.g., unipolar, bipolar, cross-chamber, etc.) by selectively closing the appropriate combination of switches. Atrial sensing circuits 82 and ventricular sensing circuits 84 may also be selectively coupled to the right atrial lead 20, coronary sinus lead 24, and the right ventricular lead 30, through the switch 74, for detecting the presence of cardiac activity in each of the four chambers of the heart. Accordingly, the atrial and ventricular sensing circuits 82 and 84 may include dedicated sense amplifiers, multiplexed amplifiers, or shared amplifiers. The switch 74 determines the "sensing polarity" of the cardiac signal by selectively closing the appropriate switches. In this way, the clinician may program the sensing polarity independent of the stimulation polarity.

Each of the atrial sensing circuit 82 or the ventricular sensing circuit 84 preferably employs one or more low power, precision amplifiers with programmable gain and automatic gain or sensitivity control, bandpass filtering, and a threshold detection circuit, to selectively sense the cardiac signal of interest. In accordance with the device, two, independent wide-band amplifiers are included in ventricular sensing circuit 84 to achieve independent sensing in each ventricle. One amplifier is used for sensing in the right ventricle and the other is used for sensing in the left ventricle. Likewise, if the device 10 is used for biatrial stimulation and sensing, atrial sensing circuit 82 includes two, wide-band amplifiers for independent sensing in the right atrium and in the left atrium. The automatic sensitivity control enables the stimulation device 10 to deal effectively with the difficult problem of sensing the low amplitude signal characteristics of atrial or ventricular fibrillation.

The outputs of the atrial and ventricular sensing circuits 82 and 84 are connected to the microcontroller 60 for triggering or inhibiting the atrial and ventricular pulse generators 70 and 72, respectively, in a demand fashion, in response to the absence or presence of cardiac activity, respectively, in the appropriate chambers of the heart. The atrial and ventricular sensing circuits 82 and 84, in turn, receive control signals over signal lines 86 and 88 from the microcontroller 60, for controlling the gain, threshold, polarization charge removal circuitry, and the timing of any blocking circuitry coupled to the inputs of the atrial and ventricular sensing circuits 82 and 84.

For arrhythmia detection, the stimulation device 10 includes an arrhythmia detector 77 that utilizes the atrial and ventricular sensing circuits 82 and 84 to sense cardiac signals, for determining whether a rhythm is physiologic or pathologic. As used herein "sensing" is reserved for the noting of an electrical signal, and "detection" is the processing of these sensed signals and noting the presence of an arrhythmia. The timing intervals between sensed events (e.g., P-waves, R-waves, and depolarization signals associated with fibrillation which are sometimes referred to as "F-waves" or "Fib-waves") are then classified by the microcontroller 60 by comparing them to a predefined rate zone limit (e.g., bradycardia, normal, low rate VT, high rate VT, and fibrillation rate zones) and various other characteristics (e.g., sudden onset, stability, physiologic sensors, and morphology, etc.), in order to determine the type of remedial therapy that is needed (e.g., bradycardia pacing, anti-tachycardia stimulation, cardioversion shocks or defibrillation shocks, collectively referred to as "tiered therapy").

Cardiac signals are also applied to the inputs of a data acquisition system 90, which is depicted as an analog-to-digital (A/D) converter for simplicity of illustration. The data acquisition system 90 is configured to acquire intracardiac electrogram (IEGM) signals, convert the raw analog data into digital signals, and store the digital signals for later processing and/or telemetric transmission to an external device 102. The data acquisition system 90 is coupled to the right atrial lead 20, the coronary sinus lead 24, and the right ventricular lead 30 through the switch bank 74 to sample cardiac signals across any pair of desired electrodes.

Advantageously, the data acquisition system 90 may be coupled to the microcontroller 60 or another detection circuitry, for detecting an evoked response from the heart 12 in response to an applied stimulus, thereby aiding in the detection of "capture". In the embodiment shown in FIG. 2, the microcontroller 60 includes an automatic capture detector 65 that searches for an evoked response signal following a stimulation pulse during an "evoked response detection window" set by timing control circuitry 79 within microcontroller 60.

The microcontroller 60 enables the data acquisition system 90 via control signal 92 to sample the cardiac signal that falls in the evoked response detection window. The sampled signal is evaluated to determine if it is an evoked response signal based on its amplitude, peak slope, or another signal feature or combination of features. The detection of an evoked response during the detection window indicates that capture has occurred.

Independent sense amplifiers for the right and left heart chambers provided by the device aid in capture verification of the right and left heart chambers during bi-chamber stimulation. A signal may be sampled from the right or left heart chamber such that an evoked response signal may be detected for verification of capture in each chamber independently and, if necessary, concurrently. Capture detection may occur on a beat-by-beat basis or on a sampled basis. When loss of capture is detected, a safety, back-up pulse is delivered shortly after the primary pulse in order to prevent asystole.

Preferably, a capture threshold search is then performed in order to re-determine the threshold and appropriately adjust the stimulation pulse output. A capture threshold search may also be performed on a periodic basis, preferably once a day during at least the acute phase (e.g., the first 30 days) and less frequently thereafter. A capture threshold search would begin at a desired starting point (either a high output level or the level at which capture is currently occurring) and continue by decreasing the output level until capture is lost. The output level is then increased again until capture is regained. The lowest output level at which sustained capture is regained is known as the capture threshold. Thereafter, the stimulation output is adjusted to a level equal to the capture threshold plus a working margin. The method for performing a threshold test in each chamber during bi-chamber stimulation will be described in detail in conjunction with FIGS. 5 and 6.

The microcontroller 60 is further coupled to a memory 94 by a suitable data/address bus 96, wherein the programmable operating parameters used by the microcontroller 60 are stored and modified, as required, in order to customize the operation of the stimulation device 10 to suit the needs of a particular patient. Such operating parameters define, for example, stimulation pulse amplitude, pulse duration, electrode polarity, rate, sensitivity, automatic features, arrhythmia detection criteria, and the amplitude, waveshape and vector of each stimulation pulse to be delivered to the patient's heart 12 within each respective tier of therapy.

Advantageously, the operating parameters of the stimulation device 10 may be non-invasively programmed into the memory 94 through a telemetry circuit 100 in telemetric communication with the external device 102, such as a programmer, transtelephonic transceiver, or a diagnostic system analyzer. The telemetry circuit 100 is activated by the microcontroller 60 by a control signal 106. The telemetry circuit 100 advantageously allows intracardiac electrograms and status information relating to the operation of the stimulation device 10 (as contained in the microcontroller 60 or memory 94) to be sent to the external device 102 through the established communication link 104.

The stimulation device 10 may further include a physiologic sensor 108, commonly referred to as a "rate-responsive" sensor because it is typically used to adjust stimulation rate according to the exercise state of the patient. However, the physiological sensor 108 may further be used to detect changes in cardiac output, changes in the physiological condition of the heart, or diurnal changes in activity (e.g., detecting sleep and wake states). Accordingly, the microcontroller 60 responds by adjusting the various stimulation parameters (such as rate, AV Delay, interventricular or interatrial delay, etc.) at which the atrial and ventricular pulse generators 70 and 72 generate stimulation pulses.

The stimulation device 10 additionally includes a power source such as a battery 110 that provides operating power to all the circuits shown in FIG. 2. For the stimulation device 10, which employs shocking therapy, the battery 110 must be capable of operating at low current drains for long periods of time, preferably less than 10 $\mu A$, and also be capable of providing high-current pulses when the patient requires a shock pulse, preferably, in excess of 2 A, at voltages above 2 V, for periods of 10 seconds or more. The battery 110 preferably has a predictable discharge characteristic so that elective replacement time can be detected.

As further illustrated in FIG. 2, the stimulation device 10 is shown to include an impedance measuring circuit 112 which is enabled by the microcontroller 60 by means of a control signal 114. The known uses for an impedance measuring circuit 112 include, but are not limited to, lead impedance surveillance during the acute and chronic phases for proper lead positioning or dislodgment; detecting operable electrodes and automatically switching to an operable pair if dislodgment occurs; measuring respiration or minute ventilation; measuring thoracic impedance for determining shock thresholds; detecting when the device has been implanted; measuring stroke volume; and detecting the opening of heart valves, etc. The impedance measuring circuit 112 is advantageously coupled to the switch 74 so that any desired electrode may be used.

If it is a function of the stimulation device 10 to operate as an implantable cardioverter/defibrillator (ICD) device, it must detect the occurrence of an arrhythmia, and automatically apply an appropriate electrical stimulation or shock therapy to the heart aimed at terminating the detected arrhythmia. To this end, the microcontroller 60 further controls a shocking circuit 116 by way of a control signal 118. The shocking circuit 116 generates shocking pulses of low (up to 0.5 Joules), moderate (0.5–10 Joules), or high (11 to 40 Joules) energy, as controlled by the microcontroller 60. Such shocking pulses are applied to the patient's heart through at least two shocking electrodes, and as shown in this embodiment, selected from the coronary sinus coil electrode 28, the RV coil electrode 36, and/or the SVC coil electrode 38 (FIG. 1). As noted above, the housing 40 may act as an active electrode in combination with the RV electrode 36, or as part of a split electrical vector using the SVC coil electrode 38 or the coronary sinus coil electrode 28.

Cardioversion shocks are generally considered to be of low to moderate energy level (so as to minimize pain felt by the patient), and/or synchronized with an R-wave and/or pertaining to the treatment of tachycardia. Defibrillation shocks are generally of moderate to high energy level (i.e., corresponding to thresholds in the range of 5–40 Joules), delivered asynchronously (since R-waves may be too disorganized), and pertaining exclusively to the treatment of fibrillation. Accordingly, the microcontroller 60 is capable of controlling the synchronous or asynchronous delivery of the shocking pulses.

Figure 3:
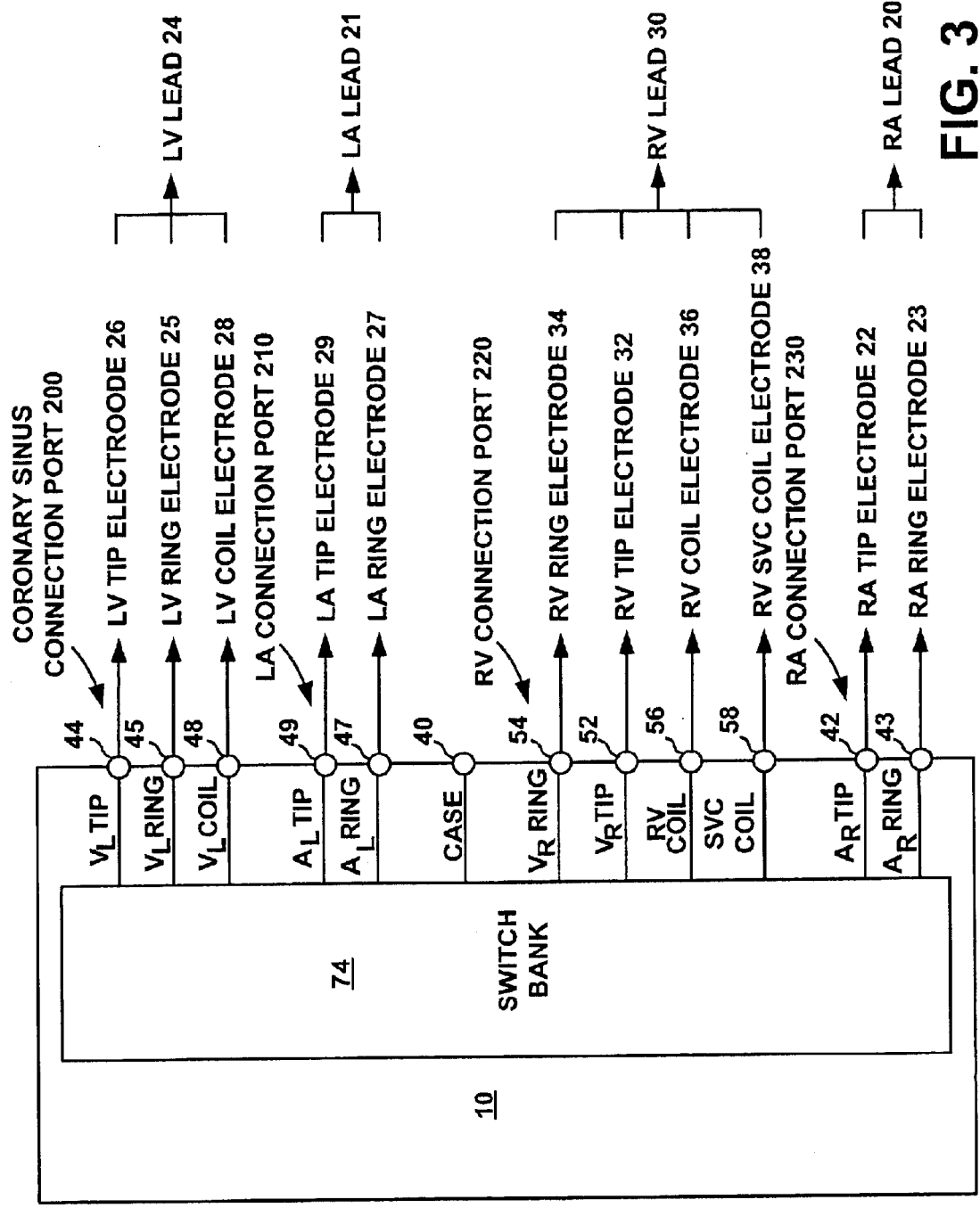
FIG. 3 is a block diagram of the stimulation device of FIG. 2, illustrating a switch with four ports for connection to four leads.

In the embodiment of FIG. 1, and as further illustrated in FIG. 3, the stimulation device 10 includes at least three connection ports 200, 220, 230. A coronary sinus connection port (CS connection port) 200 accommodates the coronary sinus lead 24 with terminals 44, 45, 46, and 48 that are associated with the left ventricular tip electrode (LVTE) 26, the left ventricular ring electrode (LVRE) 25, the left atrial ring electrode (LARE) 27, and the left atrial coil electrode (LACE) 28, respectively.

A right ventricular connection port (RV connection port) 220 accommodates the right ventricular lead 30 with terminals 52, 54, 56, 58 that are associated with the right ventricular tip electrode (RVTE) 32, the right ventricular ring electrode (RVRE) 34, the right ventricular coil electrode (RVCE) 36, and the SVC coil electrode (SVCCE) 38, respectively.

A right atrial connection port (RA connection port) 230 accommodates the right atrial lead 20 with terminals 42, 43 that are associated with the right atrial tip electrode (RATE) 22 and the right atrial ring electrode (RARE) 23, respectively.

It is recognized that numerous variations exist in which combinations of unipolar, bipolar and/or multipolar leads may be positioned at desired locations within the heart in order to provide bi-chamber or multichamber stimulation. The illustrated embodiments of the device provide for the flexibility of independent stimulation and/or sensing in multiple heart chambers by providing a cardiac stimulation device that includes multiple connection ports with unique terminals for the electrode(s) associated with each heart chamber such that the electrodes may be selectively connected to independent sensing and output circuitry using switch 74. As such, stimulation and sensing sites are not obligatorily coupled together by adapters or hardwiring within the stimulation device that would otherwise preclude independent sensing and stimulation of each chamber during either bi-chamber or multichamber stimulation.

Figure 4:
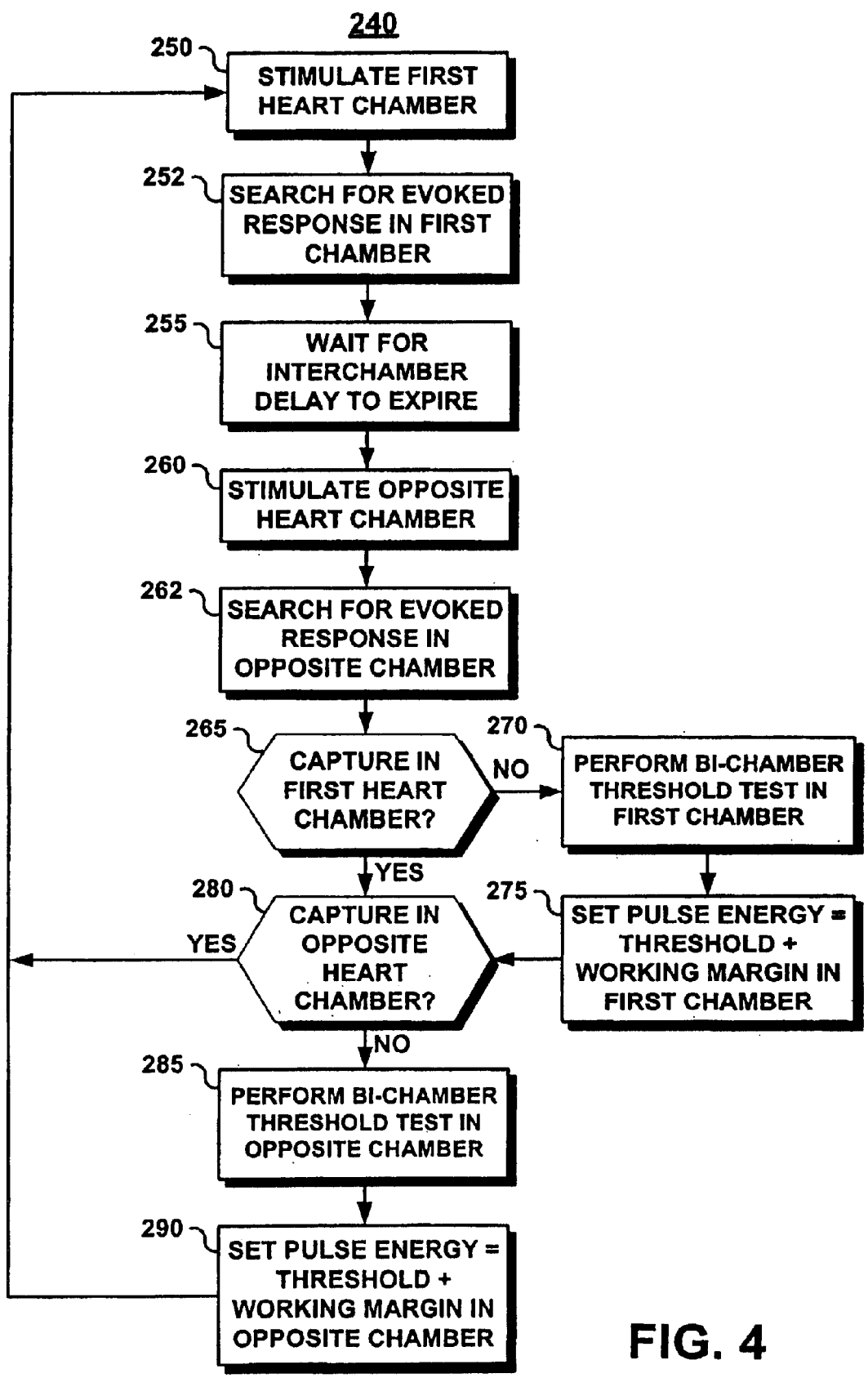
FIG. 4 is a flow chart illustrating a method implemented by the device of FIG. 2 for performing bi-chamber stimulation and automatic capture.

In FIG. 4, a process 240 is shown to illustrate an overview of the operation implemented in one embodiment of the device 10, for performing independent biatrial or biventricular stimulation and automatic capture verification. In this flow chart, and the other flow charts described herein, the various algorithmic steps are summarized in individual "blocks". Such blocks describe specific actions or decisions that must be made or carried out as the algorithm proceeds. Where a microcontroller (or equivalent) is employed, the flow charts presented herein provide the basis for a "control program" that may be used by such a microcontroller (or equivalent) to effectuate the desired control of the stimulation device. Those skilled in the art may readily write such a control program based on the flow charts and other descriptions presented herein.

At step 250 of process 240 (FIG. 4), a stimulation pulse is delivered to a heart chamber, either left or right, from the appropriate output channel of device 10. At step 252, an automatic capture detector 65 (FIG. 2) searches for an evoked response signal during an evoked response detection window.

This evoked response detection window follows the stimulation pulse delivered to the first heart chamber and is advantageously within the interchamber delay, prior to stimulating in the opposite heart chamber, such that the local evoked response in the first heart chamber can be detected without interference of the stimulation pulse in the opposite heart chamber. The evoked response signal may be sensed using the same electrodes used for stimulation, or different electrodes located near the stimulation electrodes.

After the interchamber delay expires at step 255, a stimulation pulse is delivered to the opposite heart chamber at step 260. At step 262, the automatic capture detector 65 searches for an evoked response signal in the opposite chamber.

In the case of biatrial stimulation, a stimulation pulse may be delivered first to the right atrium, followed by an interatrial delay and a stimulation pulse to the left atrium using independent atrial output channels included in atrial pulse generator 70. The evoked response signals are sensed using independent amplifiers included in atrial sensing circuit 82.

Likewise, a stimulation pulse delivered first to a ventricle would be followed by an interventricular delay and a stimulation pulse to the opposite ventricle using independent ventricular output channels included in ventricular pulse generator 72. The evoked response signals in each ventricle would be sensed using independent sense amplifiers included in ventricular sensing circuit 84. The interchamber delays are preferably programmable settings, typically on the order of 30 ms.

At decision step 265, the automatic capture detector 65 determines if capture was verified in the first chamber stimulated by the detection of an evoked response at step 252. If not, a threshold test is performed in that chamber at step 270. One method for performing a threshold test during bi-chamber stimulation will be fully described in conjunction with FIG. 5.

After re-determining the capture threshold, the stimulation pulse energy used for stimulating the first chamber may be adjusted at step 275. Typically the pulse energy is set equal to the capture threshold plus a working margin on the order of 0.25 V.

At decision step 280, the automatic capture detector 65 determines if capture was verified in the opposite chamber by the detection of an evoked response at step 262. If so, bi-chamber stimulation may continue at the programmed settings by returning to step 250. If capture is not verified in the opposite heart chamber, a threshold test is performed in that chamber at step 285.

The stimulation pulse energy used for stimulation in the opposite chamber is adjusted according to the capture threshold found in that chamber at step 290. Bi-chamber stimulation then continues, by returning to step 250, using right and left chamber stimulation pulse energy settings that have been automatically programmed according to the capture thresholds of the respective heart chambers.

Thus, independent stimulation of right and left heart chambers is performed according to the capture threshold of each chamber. Sensing of a local evoked response verifies capture of each of the right and left heart chambers. If loss of capture is detected in either chamber, a threshold test is performed in that chamber according to the bi-chamber threshold test to be described in conjunction with FIG. 5.

Figure 5:
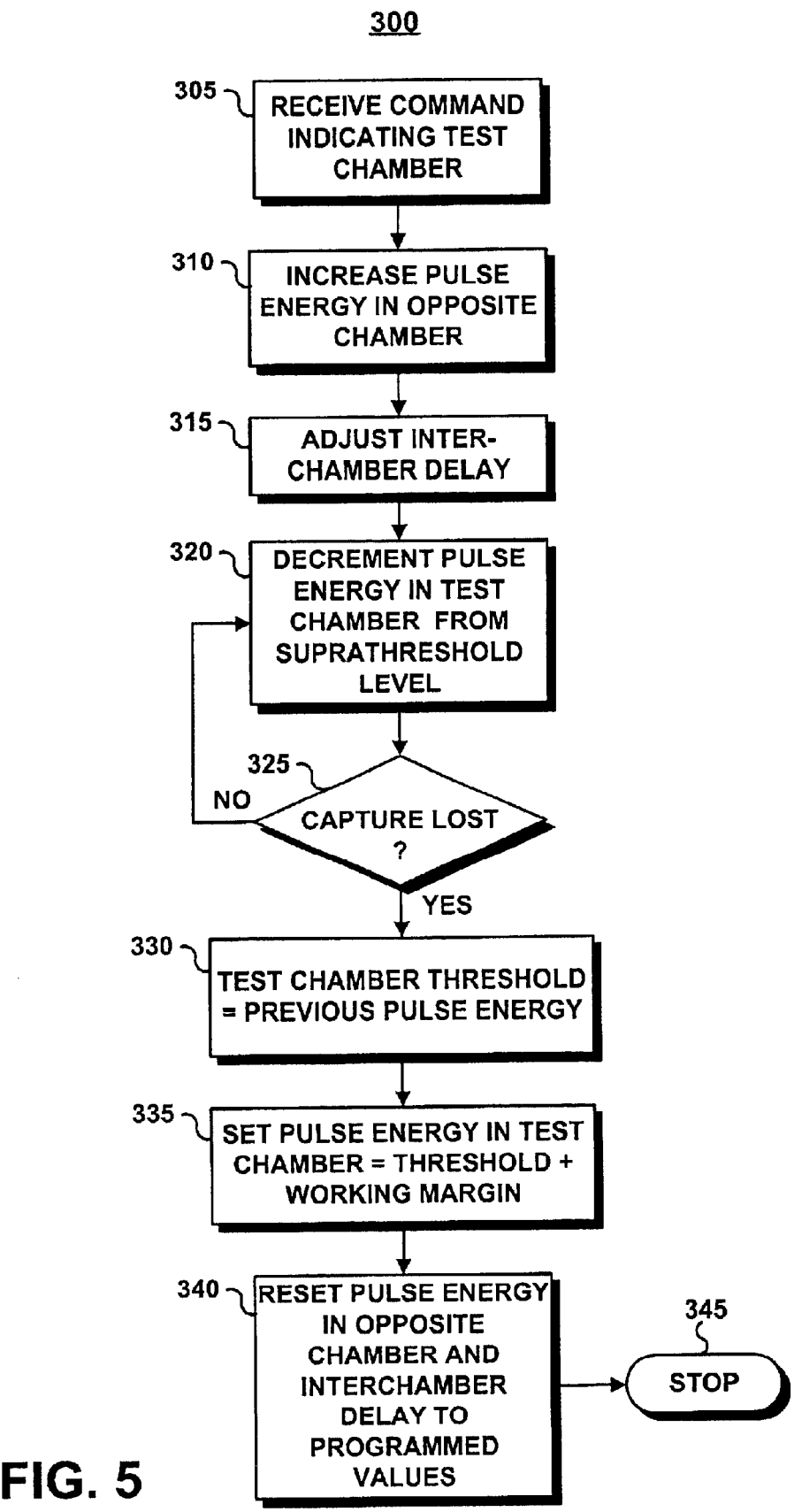
FIG. 5 is a flow chart illustrating a method implemented by the device of FIG. 2 for performing a threshold test during bi-chamber stimulation.

In FIG. 5, a process 300 illustrates an overview of the operation implemented in a preferred embodiment of the device 10, for performing threshold tests during bi-chamber stimulation. A threshold test may be performed in response to a loss of capture as described in connection with process 240 of FIG. 4, or it may be performed on a periodic basis.

At step 305 of FIG. 5, the atrial or ventricular chamber to undergo a threshold test is identified. That chamber may be either the left or right chamber, selected in either order, during a periodic threshold test, or is the chamber in which loss of capture has been detected during bi-chamber stimulation.

At step 310, the stimulation pulse energy to the opposite chamber (not being tested) is increased, preferably to approximately 1.5 times the currently programmed pulse energy for that chamber. For example, if a threshold test is performed in the right chamber, the left chamber stimulation pulse energy is increased at step 310. This step 310 of increasing pulse energy in the opposite chamber ensures continued, regular capture of the left chamber during threshold testing in the right chamber, or vice versa.

At step 315, the interchamber delay is adjusted such that the opposite chamber is not stimulated during the evoked response detection window that will be applied following delivery of a test stimulation pulse in the first chamber. If threshold testing is being performed during biatrial stimulation, the interatrial delay is adjusted. If threshold testing during biventricular stimulation is being performed, the interventricular delay is adjusted.

The delay is adjusted such that the chamber to be tested is stimulated first, preferably followed by a lengthened delay period after which stimulation to the opposing chamber is delivered. The lengthened delay will not only prevent stimulation of the opposing chamber during evoked response sensing in the first chamber but also prevents a depolarization in the opposing chamber from propagating to the test chamber during the evoked response detection window, which would likely produce erroneous threshold test results.

At step 320, the stimulation pulse energy in the test chamber is decreased by predetermined steps, typically 0.25 or 0.5 Volts, until capture is lost as determined at decision step 325. The stimulation pulse energy starts at a level certain to achieve capture: either the currently programmed setting in the case of a periodic threshold test or, in the case of a detected loss of capture, a predetermined maximum setting.

Once loss of capture is detected at decision step 325, the capture threshold is identified at step 330 as the previous, lowest pulse energy setting at which capture was maintained. The stimulation pulse energy for the tested chamber is adjusted at step 335 to be equal to the newly determined capture threshold plus a working margin, typically 0.25 Volts.

At step 340, the stimulation pulse energy for the opposite chamber is reset to the programmed value, and the interchamber delay is reset to the programmed setting. The threshold test is thus terminated at step 345.

Alternatively, the threshold test may be performed by beginning at a sub-threshold stimulation level and then incrementally increasing the energy level until the chamber being tested is captured. The stimulation pulse energy is then preferably set to be equal to the capture threshold plus a working margin, e.g. 0.25 Volts.

Figure 6:
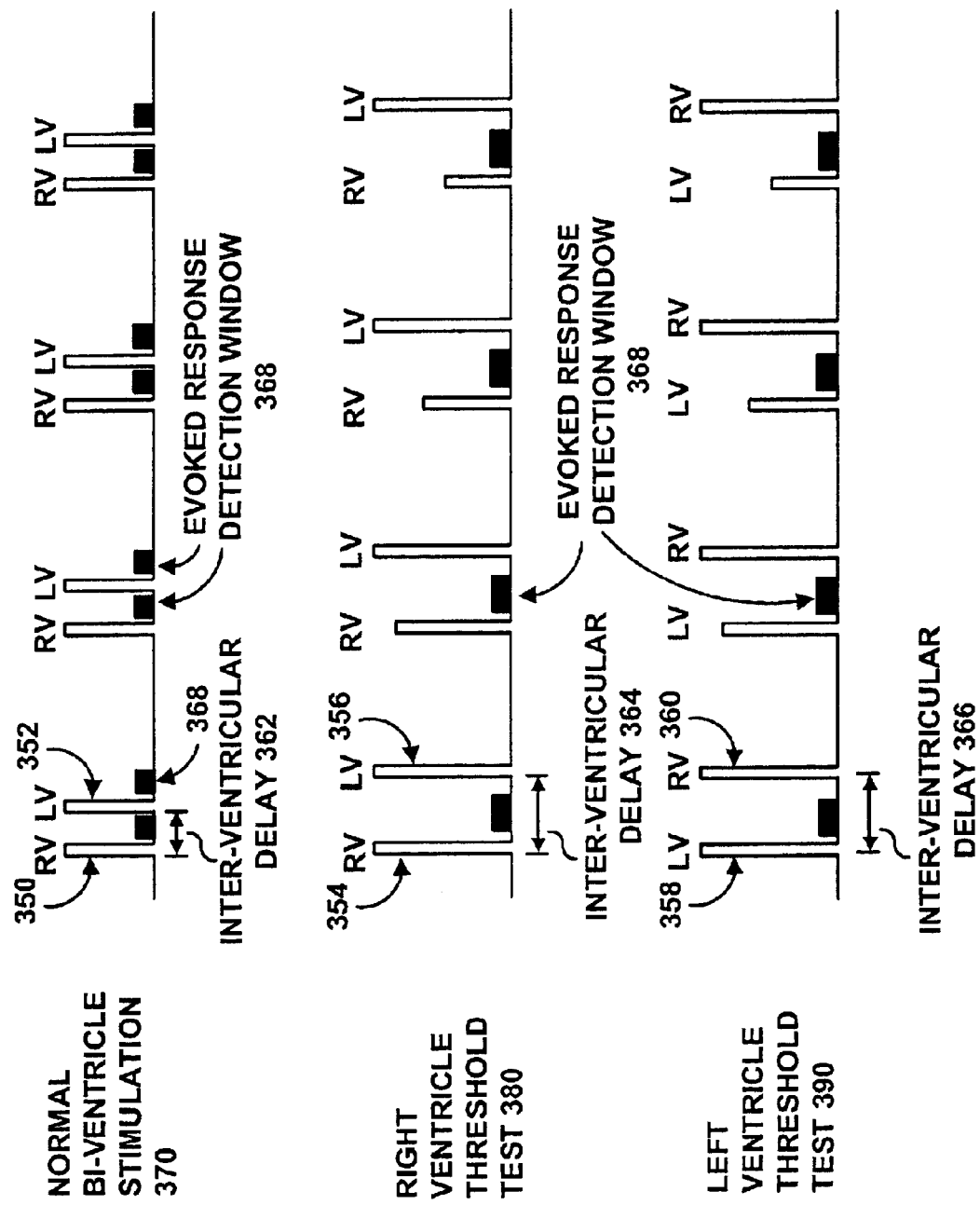
FIG. 6 is an illustration of the output generated by the device of FIG. 2 during the implementation of the method of FIG. 5.

The output of device 10 during the implementation of method 300 of FIG. 5 is illustrated in FIG. 6. In this example, biventricular stimulation is being performed, but similar operations may be performed in the atria. The outputs from the independent right and left ventricular output channels are shown on one trace for the sake of convenience.

The top trace depicts a normal bi-ventricular stimulation mode 370, wherein the right ventricular stimulation pulse 350 and the left ventricular stimulation pulse 352 are separated by an interventricular delay 362. In this example, the right ventricular stimulation pulse and the left ventricular stimulation pulse are shown having equal pulse width and pulse amplitude. However, the pulse width or pulse amplitude may be adjusted in the independent output channels to provide stimulation pulses according to the capture threshold of each chamber.

Following each ventricular stimulation pulse 350 and 352, is an evoked response detection window 368. The automatic capture detector 65 searches for a local evoked response in the stimulated chamber during the evoked response detection window. An evoked response detection window may follow every stimulation pulse as illustrated in FIG. 6, to allow capture verification on a beat-by-beat basis. Alternatively, capture verification may be performed less frequently, on a periodic or sampled basis.

In the second trace, the outputs of the left and right ventricular output channels are shown during a right ventricular threshold test 380. The left ventricular stimulation pulse 356 is increased, in this example by increasing the pulse amplitude to 1.5 times the pulse amplitude during normal stimulation 370. The interventricular delay 364 is lengthened such that the left ventricle is stimulated at an extended delay after the right ventricle.

The evoked response detection window 368 is set during the interventricular delay 364 such that an evoked response may be detected in the right chamber prior to delivering a stimulation pulse to the left ventricle, thus avoiding interference from the left ventricular stimulation pulse or depolarization. The right ventricular stimulation pulse 354 can be seen to undergo a progressive decrease in pulse amplitude beginning from a predetermined maximum pulse amplitude. During an actual threshold test, the right ventricular pulse amplitude would be decreased until loss of capture is detected, i.e., no evoked response detected during the evoked response detection window.

One advantage of this bi-chamber threshold test method is that when loss of capture occurs in the right ventricle, no safety back-up stimulation pulse is needed to depolarize the right ventricle. This is because the stimulation pulse delivered to the left ventricle is set to guarantee capture of the left ventricle which will produce a depolarization wave that will be conducted to the right ventricle and cause depolarization of the previously non-captured right ventricle. Therefore, in this embodiment, left ventricular stimulation at an increased pulse energy is committed to during the right ventricular threshold test and vice versa. Alternatively, the device 10 may be programmed to deliver the back up pulse in the right ventricle to maintain interventricular synchronization for the hemodynamic benefit of the patient.

In an alternative embodiment, stimulation to the opposite chamber could be inhibited upon sensing an intrinsic depolarization in the opposite chamber. If the conduction time between the right and left chambers is shorter than the lengthened interchamber delay, a test pulse that captures the tested chamber will produce a depolarization that is conducted to the opposite chamber causing depolarization of the opposite chamber as well.

If this depolarization is sensed by the device 10, the stimulation pulse scheduled to be delivered to the opposite chamber at the end of the interchamber delay may be inhibited. If no depolarization is sensed, the opposite chamber is stimulated at an increased pulse energy expected to guarantee capture that will further be conducted to the tested chamber if the tested chamber was not captured by the test pulse.

In the third trace, a left ventricular threshold test 390 is performed. In this test, the inter-ventricular delay 366 is adjusted such that the right ventricular stimulation pulse 360 is delivered at an extended delay after the left ventricular stimulation pulse 358. The right ventricular stimulation pulse 360 is set at 1.5 times its programmed pulse amplitude. The left ventricular stimulation pulse 358 begins at a high level and is seen to be progressively decreased. During an actual threshold test, the left ventricular pulse amplitude would be decreased until loss of capture is detected. When loss of capture occurs in the left ventricle, a depolarization from the right ventricle will propagate to the left ventricle and cause depolarization precluding the need for a safety back-up pulse in the left ventricle. The backup pulse in the left ventricle may be programmed for delivery in the event of left-ventricular loss-of-capture.

Figure 7:
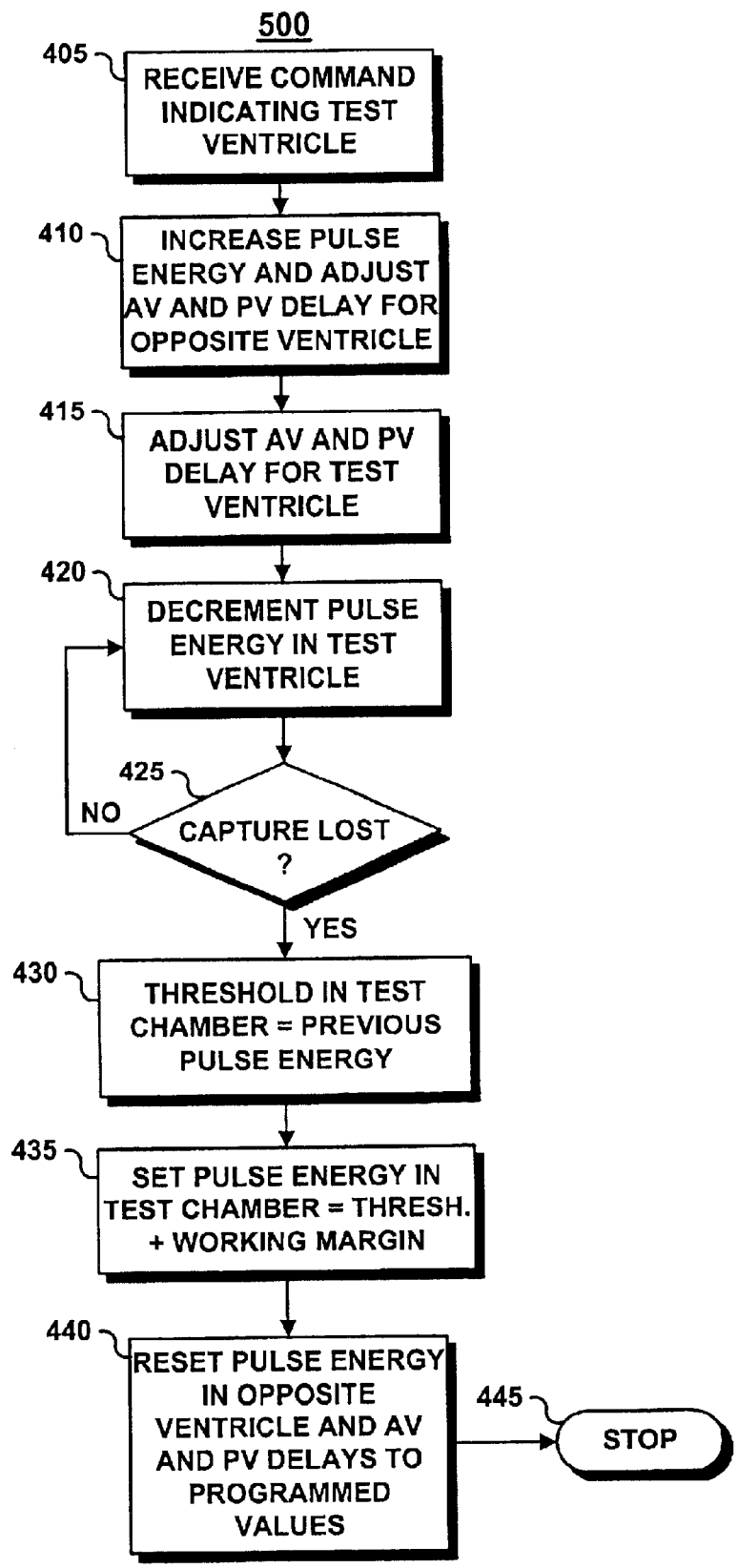
FIG. 7 is a flow chart illustrating a method implemented by the device of FIG. 2 for performing a ventricular threshold test during multichamber stimulation.

In FIG. 7, a process 500 is shown describing an overview of the operations implemented in one embodiment of the device 10 for performing ventricular threshold tests during multichamber stimulation. At step 405, microcontroller 60 identifies the ventricle, left or right, in which a threshold test will be performed. At step 410, the stimulation pulse energy applied in the opposing ventricle (not being tested) is set to a temporary high level, preferably to 1.5 times the currently programmed setting. This increase in pulse energy ensures capture of the opposing ventricle while testing is being performed in the first ventricle.

The AV and PV delays associated with the opposing ventricle are also temporarily adjusted at step 410. At step 415, the AV and PV delays associated with the ventricle undergoing a threshold test are temporarily shortened, preferably to 25 ms and 50 ms respectively. For example, if a right ventricular threshold test is to be performed, the left AV delay and the left PV delay are temporarily lengthened to predetermined intervals; the right AV delay and right PV delay are shortened to 25 ms and 50 ms, respectively. The adjustment of the AV and PV delays to the opposing ventricle and the shortened AV and PV delays in the test ventricle prevent a conducted depolarization from the opposing ventricle from interfering with evoked response detection in the tested ventricle. The shortened AV and PV delays in the test ventricle also ensure stimulation of the test ventricle prior to an intrinsic depolarization due to conduction of the atrial depolarization to the ventricle. Furthermore, the shortened AV and PV delays in the test chamber avoid fusion, which would confound the threshold test results. Fusion occurs when a stimulation pulse is delivered approximately at the same time as an intrinsic depolarization, causing a distorted depolarization signal.

At step 420, the stimulation pulse energy is progressively decreased from a level known to evoke capture, either the currently programmed setting in the case of a periodic threshold test or, in the case of loss of capture, a predetermined maximum setting, until loss of capture is detected at decision step 425. Once capture is lost, the capture threshold is identified as the lowest pulse energy at which capture was maintained at step 430. Hence, at step 435, the stimulation pulse energy for the tested ventricle is adjusted to the newly determined threshold plus a working margin, typically 0.25 Volts. At step 440 the AV and PV delays associated with both ventricles are reset to the programmed settings, and the pulse energy in the opposing chamber is reset to its programmed setting. At step 445, the threshold test is terminated.

The output of device 10 during independent stimulation of all four heart chambers and during the ventricular threshold testing operations summarized in the flow chart of FIG. 7 is illustrated by the diagrams of FIG. 8. The normal four-chamber stimulation mode 450 is represented by the top two traces depicting atrial output 452 and ventricular output 456. The atrial output 452 from two independent atrial channels, stimulating the right and left atria, is shown on one trace for the sake of convenience. The right atrial and left atrial stimulation pulses 462 and 464, respectively, are shown separated in time by an interatrial delay 454.

The ventricular output 456 from two independent ventricular channels is also shown on one trace, for the sake of convenience. The right ventricular stimulation pulse 466 can be seen to occur after the right atrial pulse 462 following a right AV delay 458. The left ventricular stimulation pulse 468 is shown to occur after the left atrial pulse 464 following a left AV delay 460.

Thus, it can be seen that stimulation of each of the four chambers may be delivered at prescribed interchamber delays for achieving a desired sequence of heart chamber contractions. Furthermore, each stimulation pulse may be followed by an evoked response detection window 492, during which no stimulation pulse is delivered to any other heart chamber, to allow beat-by-beat capture verification of each chamber.

The operation of device 10 during a ventricular threshold test 470 is illustrated by the two lower traces of FIG. 8. In the example shown, a threshold test is to be performed in the left ventricle. The atrial output 480 from the two independent atrial channels remains the same as during normal stimulation mode 450.

The stimulation pulse output to the right ventricle 476 is temporarily increased to an amplitude 1.5 times greater than the amplitude during the normal stimulation mode 450. The right AV delay 478 is increased to a predetermined setting. The left AV delay 490 is shortened, preferably to 25 ms, to avoid fusion.

Thus, the left ventricular stimulation pulse 474 is seen to be delivered much earlier than the right ventricular stimulation pulse 476 so that a stimulation pulse or a conducted depolarization from the right ventricle will not interfere with evoked response detection in the left ventricle during the evoked response detection window 492.

The left ventricular stimulation pulse 474 is seen to start at an initially high amplitude and progressively decrease in amplitude during the threshold test. Four decreasing pulses are shown for the sake of illustration, however, once loss of capture is detected, the left ventricular capture threshold would be identified, and the threshold test would be complete. Similar procedures may be performed in the right ventricle for determining a right ventricular capture threshold. Likewise, right and left atrial capture thresholds may be determined according to the operations described previously in conjunction with FIG. 5.

Thus, the device and method provide for automatic and separate adjustment of the stimulation pulse energy for each heart chamber based on an automatically determined capture threshold for each chamber being stimulated.

In an alternative embodiment, stimulation pulses may be delivered concurrently to the left and right chambers, each followed by an appropriately timed evoked response detection window during which the local evoked response is sensed in each chamber individually using independent sense amplifiers. The evoked response detection windows in this embodiment are limited to the time immediately after the stimulation pulse during which a local evoked response is expected. The evoked response detection windows would be kept shorter than the interchamber conduction time such that if one chamber is captured and one isn't, a conducted depolarization is not detected in the non-captured chamber and mistaken for a capture detection.

Thus, a system and method for providing independent stimulation and sensing in each heart chamber during bi-chamber or multichamber stimulation therapy has been described in which each chamber is stimulated according to its own capture threshold, thus conserving battery energy.

Methods provided herein for performing threshold tests in each chamber independently allow for a determination of capture threshold for each chamber while minimizing the need for safety back-up pulses by ensuring capture of the opposing chamber during a threshold test.

Furthermore, independent capture verification of each chamber is made possible through independent sensing channels, thus ensuring that precisely timed stimulation pulses effectively produce a desired synchronization of heart chambers. While detailed descriptions of specific embodiments of the device and method have been provided, it would be apparent to those reasonably skilled in the art that numerous variations of the methods described herein are possible in which the concepts of the device and method may readily be applied. The descriptions provided herein are for the sake of illustration and are not intended to be exclusive.

What is claimed is:

1. A method for bi-chamber stimulation and automatic capture detection for use in a cardiac stimulation device, the method comprising:

delivering stimulation pulses to a first cardiac chamber and to an opposite chamber based on capture thresholds of the respective cardiac chambers and based on respective interchamber delays;

verifying capture of the respective cardiac chambers; and if capture is not verified in the first cardiac chamber, performing a threshold test in the first cardiac chamber while stimulating the opposite cardiac chamber at an increased pulse energy and at an extended interchamber delay.

2. The method according to claim 1, wherein verifying capture of the first cardiac chamber comprises:

setting a first evoked response detection window following a delivered stimulation pulse to the first cardiac chamber; and detecting an evoked response signal during the first evoked response detection window.

3. The method according to claim 1, further comprising verifying capture of the opposite cardiac chamber by:

setting a second evoked response detection window following a delivered stimulation pulse to the opposite cardiac chamber; and detecting an evoked response signal during the second evoked response detection window.

4. The method according to claim 1, wherein performing the threshold test in the first cardiac chamber comprises:

stimulating the first cardiac chamber at a number of test pulse energy settings;

setting a first evoked response detection window following delivery of a test pulse to the first cardiac chamber;

stimulating the opposite cardiac chamber at a pulse energy that evokes capture of the opposite chamber with high probability; and setting a lowest test pulse energy at which an evoked response is consistently detected during the first evoked response detection window as the capture threshold of the first cardiac chamber.

5. The method according to claim 4, wherein stimulating the opposite cardiac chamber comprises stimulating the opposite cardiac chamber at an adjusted interchamber delay to avoid stimulation of the opposite cardiac chamber during the first evoked response detection window; and wherein, if a threshold test pulse does not capture the first cardiac chamber, stimulation of the opposite cardiac chamber results in a depolarization that propagates to and depolarizes the first cardiac chamber.

6. The method according to claim 5, further comprising inhibiting delivery of a stimulation pulse to the opposite cardiac chamber if a depolarization of the first cardiac chamber is detected prior to the expiration of the adjusted interchamber delay.

7. The method according to claim 4, wherein performing the threshold test in the first cardiac chamber comprises:

stimulating the opposite cardiac chamber at a number of test pulse energy settings;

setting a second evoked response detection window following delivery of a test pulse;

stimulating the first cardiac chamber at a pulse energy that evokes capture of the first chamber with high probability;

setting a lowest test pulse energy at which an evoked response is consistently detected during the second evoked response detection window as the capture threshold of the opposite cardiac chamber.

8. The method according to claim 7, further comprising stimulating the first cardiac chamber at an adjusted interchamber delay to avoid stimulation of the first cardiac chamber during the second evoked response detection window.

9. The method according to claim 4, further comprising automatically adjusting a stimulation pulse energy to be delivered in the first cardiac chamber based on the capture threshold for the first cardiac chamber.

10. The method according to claim 9, further comprising automatically adjusting a stimulation pulse energy to be delivered in the opposite cardiac chamber based on the capture threshold for the opposite cardiac chamber.

11. The method according to claim 4, wherein stimulating the opposite cardiac chamber comprises delivering a stimulation pulse following a predetermined interchamber delay.

12. The method according to claim 1, wherein delivering the stimulation pulse to the first cardiac chamber comprises delivering the stimulation pulse to a right atrium; and further comprising delivering a stimulation pulse to a left atrium.

13. The method according to claim 1, wherein delivering the stimulation pulse to the first cardiac chamber comprises delivering the stimulation pulse to a left atrium; and further comprising delivering a stimulation pulse to a right atrium.

14. The method according to claim 1, wherein delivering the stimulation pulse to the first cardiac chamber comprises delivering the stimulation pulse to a right ventricle; and further comprising delivering a stimulation pulse to a left ventricle.

15. The method according to claim 1, wherein delivering the stimulation pulse to the first cardiac chamber comprises delivering the stimulation pulse to a left ventricle; and further comprising delivering a stimulation pulse to a right ventricle.

16. The method according to claim 1, wherein performing the threshold test comprises:

concurrently stimulating the first cardiac chamber and the opposite cardiac chamber at a number of test pulse energy settings;

setting a first evoked response detection window for detecting an evoked response in the first cardiac chamber;

setting a second evoked response detection window for detecting an evoked response in the opposite cardiac chamber;

setting a lowest test pulse energy at which an evoked response is consistently detected during the first evoked response detection window as the capture threshold of the first cardiac chamber; and setting the lowest test pulse energy at which an evoked response is consistently detected during the second evoked response detection window as the capture threshold of the opposite cardiac chamber.

17. A cardiac stimulation device for bi-chamber stimulation and automatic capture testing, the device comprising:

a pulse generator that delivers stimulation pulses to a first cardiac chamber and to an opposite cardiac chamber based on capture thresholds of the respective cardiac chambers;

an automatic capture detector connected to the pulse generator, the detector being operative to verify capture of the respective cardiac chambers;

wherein if the automatic capture detector confirms loss of capture in the first cardiac chamber, the automatic capture detector is operative to perform a threshold test in the first cardiac chamber while stimulating the opposite cardiac chamber at an extended interchamber delay and at an increased pulse energy; and wherein if the automatic capture detector confirms loss of capture in the opposite cardiac chamber, the automatic capture detector is operative to perform a threshold test in the opposite cardiac chamber while stimulating the first cardiac chamber at an extended interchamber delay and at an increased pulse energy.

18. The device according to claim 17, further comprising a timing control circuit that sets a first evoked response detection window following a delivered stimulation pulse to the first cardiac chamber; and a sensor that detects an evoked response signal during the first evoked response detection window.

19. The device according to claim 18, wherein the timing control circuit sets a second evoked response detection window following a delivered stimulation pulse to the opposite cardiac chamber; and a sensor that detects an evoked response signal during the second evoked response detection window.

20. The device according to claim 17, wherein the pulse generator stimulates the first cardiac chamber at a number of test pulse energy settings;

further comprising a timing control circuit that sets a first evoked response detection window following delivery of a test pulse to the first cardiac chamber;

wherein the pulse generator stimulates the opposite cardiac chamber at a pulse energy that evokes capture of the opposite chamber with high probability; and wherein the automatic capture detector sets a lowest test pulse energy at which an evoked response is consistently detected during the first evoked response detection window as the capture threshold of the first cardiac chamber.

21. The device according to claim 20, wherein the pulse generator stimulates the opposite cardiac chamber at an adjusted interchamber delay to avoid stimulation of the opposite cardiac chamber during the first evoked response detection window.

22. The device according to claim 21, further comprising a controller that inhibits delivery of a stimulation pulse to the opposite cardiac chamber if a sensor detects a depolarization of the first cardiac chamber prior to the expiration of the adjusted interchamber delay.

23. The device according to claim 20, wherein the pulse generator stimulates the opposite cardiac chamber at a number of test pulse energy settings;

wherein the timing control circuit sets a second evoked response detection window following delivery of a test pulse;

wherein the pulse generator stimulates the first cardiac chamber at a pulse energy that evokes capture of the first chamber with high probability; and wherein the automatic capture detector sets a lowest test pulse energy at which an evoked response is consistently detected during the second evoked response detection window as the capture threshold of the opposite cardiac chamber.

24. The device according to claim 23, wherein the pulse generator stimulates the first cardiac chamber at an adjusted interchamber delay to avoid stimulation of the first cardiac chamber during the second evoked response detection window.

25. The device according to claim 20, further comprising a controller that automatically adjusts a stimulation pulse energy to be delivered in the first cardiac chamber based on the capture threshold for the first cardiac chamber.

26. The device according to claim 25, wherein the controller automatically adjusts a stimulation pulse energy to be delivered in the opposite cardiac chamber based on the capture threshold for the opposite cardiac chamber.

27. The device according to claim 20, wherein the pulse generator delivers a stimulation pulse to the opposite cardiac chamber following a predetermined interchamber delay.

28. The device according to claim 17, wherein the first cardiac chamber is a right atrium and the opposite cardiac chamber is a left atrium.

29. The device according to claim 17, wherein the first cardiac chamber is a left atrium and the opposite cardiac chamber is a right atrium.

30. The device according to claim 17, wherein the first cardiac chamber is a right ventricle and the opposite cardiac chamber is a left ventricle.

31. The device according to claim 17, wherein the first cardiac chamber is a left ventricle and the opposite cardiac chamber is a right ventricle.

32. The device according to claim 20, wherein the interchamber delay is approximately 30 ms.

33. The device according to claim 26, wherein the stimulation pulse energy delivered to the opposite cardiac chamber is approximately 1.5 times greater than a programmed stimulation pulse energy setting.

34. A cardiac stimulation device for bi-chamber stimulation and automatic capture testing, the device comprising:

means for stimulating a first cardiac chamber and an opposite cardiac chamber;

means for verifying capture of the respective cardiac chambers;

means for performing a threshold test in the first cardiac chamber while stimulating the opposite cardiac chamber at an extended interchamber delay and at an increased pulse energy if the first cardiac chamber is not captured; and means for performing a threshold test in the opposite cardiac chamber while stimulating the first cardiac chamber at an extended interchamber delay and at an increased pulse energy if the opposite cardiac chamber is not captured.

35. The device according to claim 34, further comprising a first means for setting a first evoked response detection window following a delivered stimulation pulse to the first cardiac chamber; and means for sensing an evoked response signal during the first evoked response detection window.

36. The device according to claim 35, further comprising a second means for setting a second evoked response detection window following a delivered stimulation pulse to the opposite cardiac chamber; and wherein the sensing means detects an evoked response signal during the second evoked response detection window.

37. The device according to claim 34, wherein the means for stimulating stimulates the first cardiac chamber at a number of test pulse energy settings;

further comprising means for setting a first evoked response detection window following delivery of a test pulse to the first cardiac chamber;

wherein the means for stimulating stimulates the opposite cardiac chamber at a pulse energy that evokes capture of the opposite chamber with high probability; and wherein the means for verifying capture sets a lowest test pulse energy at which an evoked response is consistently detected during the first evoked response detection window as the capture threshold of the first cardiac chamber.

38. The device according to claim 37, wherein the means for stimulating stimulates the opposite cardiac chamber at an adjusted interchamber delay to avoid stimulation of the opposite cardiac chamber during the first evoked response detection window.

39. The device according to claim 38, further comprising means for inhibiting delivery of a stimulation pulse to the opposite cardiac chamber if a sensor detects a depolarization of the first cardiac chamber prior to the expiration of the adjusted interchamber delay.

40. The device according to claim 37, wherein the means for stimulating stimulates the opposite cardiac chamber at a number of test pulse energy settings;

further comprising means for setting a second evoked response detection window following delivery of a test pulse;

wherein the means for stimulating stimulates the first cardiac chamber at a pulse energy that evokes capture of the first chamber with high probability; and wherein the means for verifying capture sets a lowest test pulse energy at which an evoked response is consistently detected during the second evoked response detection window as the capture threshold of the opposite cardiac chamber.

\* \* \* \* \*